US008614355B2

(12) United States Patent
Wolf et al.

(10) Patent No.: US 8,614,355 B2
(45) Date of Patent: Dec. 24, 2013

(54) CATALYST AND PROCESS FOR HYDROGENATING ORGANIC COMPOUNDS

(75) Inventors: Aurel Wolf, Wülfrath (DE); Volker Michele, Köln (DE); Jens Aβmann, Hilden (DE); Leslaw Mleczko, Dormagen (DE)

(73) Assignee: Bayer Technology Services GmbH, Leverkusen (DE)

( * ) Notice: Subject to any disclaimer, the term of this patent is extended or adjusted under 35 U.S.C. 154(b) by 160 days.

(21) Appl. No.: 12/997,301

(22) PCT Filed: Jun. 3, 2009

(86) PCT No.: PCT/EP2009/003950
§ 371 (c)(1),
(2), (4) Date: Feb. 17, 2011

(87) PCT Pub. No.: WO2009/149849
PCT Pub. Date: Dec. 17, 2009

(65) Prior Publication Data
US 2011/0130592 A1    Jun. 2, 2011

(30) Foreign Application Priority Data

Jun. 12, 2008    (DE) .......................... 10 2008 028 070

(51) Int. Cl.
*C07C 209/00*    (2006.01)
(52) U.S. Cl.
USPC ............................ 564/420; 564/415; 564/416
(58) Field of Classification Search
None
See application file for complete search history.

(56) References Cited

U.S. PATENT DOCUMENTS

2006/0142148 A1    6/2006 Ma et al.
2007/0275160 A1    11/2007 Maldonado

FOREIGN PATENT DOCUMENTS

WO    WO2007093337    *   8/2007

OTHER PUBLICATIONS

XP002544138, Nitrogen-Containing Carbon Nanotubes as Solid Base Catalysts, S. Van Dommele, et al., Chom. Commun., pp. 4859-4861, 2006.
XP022442518, Tuning Nitrogen Functionalities in Catalytically Grown Nitrogen-Containing Carbon Nanotubes, Van Dommele et al., Carbon Elsvier, vol. 46, No. 1, pp. 138-148, Nov. 2007.
XP022157996, Synthesis of Nitrogen-Containing Carbon Nanofibers by Catalytic Decomposition of Ethylene/Ammonia Mixture, Shalagina et al., Carbon Elsevier, vol. 45, No. 9, pp. 1808-1820, Jul. 2007.
XP005893149, Oxygen Reduction Reaction Activity and Surface Properties of Nanostructured Nitrogen-Containing Carbon, Matter et al., Journal of Molecular Catalysis, vol. 264, No. 1-2, pp. 73-81, Feb. 2007.
XP004692174, Nitrobenzene Hydrogenation with Carbon Nanotube-Supported Platinum Catalyst Under Mild Conditions, Li C-H et al., Journal of Molecular Catalysis, vol. 226, No. 1, pp. 101-105, Feb. 2005.
Effect of Microstructures of Pt Catalysts Supported on Carbon Nanotubes (CNTs) and Activated Carbon (AC) for Nitrobenzene Hydrogenation, Yun Zhao et al., Materials Chemistry and Physics, vol. 103, pp. 225-229, 2007.
Helical Mictrtubules of Graphitic Carbon, Sumio Lijimi, Letters to Nature, vol. 354, pp. 56-58, Nov. 1991.
Synthesis of Heterogeneous Base Catalysts: Nitrogen Containing Carbon Nanotubes, S. Van Dommele, et al., Scientific Bases for the Preparation of Heterogeneous Catalysts, pp. 29-36, 2006.
Handbook of Heterogeneous Catalytic Hydrogenation for Organic Synthesis, Shigeo Nishimura, Tokyo University of Agriculture and Technology, 2001, pp. 1 to 52.

* cited by examiner

*Primary Examiner* — Clinton Brooks
(74) *Attorney, Agent, or Firm* — Norris McLaughlin & Marcus PA

(57)    ABSTRACT

The invention relates to a catalyst and to a process for hydrogenating organic compounds. In particular, the invention is directed to a process and catalyst for hydrogenating organic compounds with hydrogen. The organic compounds are subjected to hydrogenation in the presence of a catalyst comprising nitrogen-doped carbon nanotubes as a catalytically active component, wherein the proportion of nitrogen in the nanotubes is in the range of from about 0.05 to 20 wt. %.

15 Claims, No Drawings

CATALYST AND PROCESS FOR HYDROGENATING ORGANIC COMPOUNDS

This application is a 371 National Phase application of PCT/EP2009/003950 filed Jun. 3, 2009, which claims priority to German application 10 2008 028 070.4 filed Jun. 12, 2008.

The invention relates to a catalyst and a process for hydrogenating organic compounds.

Hydrogenations are a transformation method which is often employed in the chemical industry for organic compounds having functional groups such as nitro, C—C double bond, carbonyl, etc., with the corresponding hydrogenation products (amines, alkanes, alcohols, etc.) being formed. The hydrogenation is generally carried out over supported noble metal catalysts (Au, Pd, Pt, Ru, etc.) or over Raney nickel (S. Nishimura, Handbook of Heterogeneous Catalytic Hydrogenation for Organic Synthesis, 2001, 2-38).

The noble metal catalysts supported on oxides (silica, alumina, titania) or activated carbon are very expensive because of the noble metals and are subject to deactivation by sintering. Raney Ni catalysts, on the other hand, are cheaper to procure but are significantly less reactive than the supported noble metal catalysts. To eleviate this disadvantage, Raney Ni catalysts are often used as finely divided powder (100-300 μm), which in turn leads to time-consuming separation of the catalyst from the reaction mixture. In addition, these catalysts are pyrophoric in air, so their handling is always complicated in terms of safety.

Processes which can reduce the required proportion of expensive noble metals using carbon nanotubes have therefore been developed. Thus, Li et. al. and Zhao et. al. disclose new types of Pt catalysts supported on carbon nanotubes for the hydrogenation of nitrobenzene (J. Molec. Cat. A: chem, 2005, 226(1), 101-105 and Mater. Chem. and Phys., 2007, 103(2-3), 225-229). In both cases, it is explained that the catalytic effect is attributable to the platinum applied to the carbon nanotubes. The carbon nanotubes as such display no significant catalytic activity. In Mater. Chem. and Phys., 2007, 103(2-3), 225-229, it is further explained that the catalysts presented are made expensive by the use of the metals. However, in both cases it is not disclosed that the carbon nanotubes used have been modified by heteroatoms or that an advantageous effect can be achieved thereby.

A similar approach is disclosed by Han et. al. (J. Molec. Cat. A: Chem, 2007, 277(1-2), 210-214 and hid. J. of Chem., Sect A., 2007, 46A(11), 1747-1752), which uses suitable bimetallic catalysts on surfaces of carbon nanotubes for hydrogenating p-/o- and m-chloronitrobenzene. There, the term bimetallic refers to the presence of further metals in addition to platinum. In particular, the use of bimetallic catalysts containing platinum, carbon nanotubes and metals selected from the group consisting of manganese, iron, cobalt, nickel and copper is disclosed. Han et al. further disclose that the pure carbon nanotubes display no catalytic effect. It is not disclosed that the carbon nanotubes used have been modified by heteroatoms.

The disclosures of the prior art in respect of hydrogenation processes relate to the use of purely graphitic catalyst materials in the form of carbon nanotubes and are characterized in that they cannot dispense with expensive noble metals (for example Pt) as catalytically active component. Only the support material has been able to be replaced. Such catalysts and processes using these therefore continue to be economically disadvantageous.

Carbon nanotubes as a modification of carbon have been generally known to those skilled in the art since 1991 (S. Iijima, Nature 354, 56-58, 1991). Since then, the term carbon nanotubes has referred to cylindrical bodies comprising carbon which have a diameter in the range from 3 to 80 nm and a length which is a multiple, by a factor of at least 10 of the diameter. These carbon nanotubes are further characterized by layers of ordered carbon atoms; the carbon nanotubes normally have a core which differs in terms of the morphology. Synonyms for carbon nanotubes are, for example, "carbon fibrils" or "hollow carbon fibers" or "carbon bamboos" (or, in the case of rolled structures) "nanoscrolls" or "Nanorolls".

It is also known that the abovementioned carbon nanotubes can be modified by heteroatoms, e.g. heteroatoms from the fifth main group (for instance nitrogen), during the process for producing them.

Van Dommele et al. and Matter et al. (S. van Dommele et al., Stud. Surf. Sci. and Cat., 2006, 162, 29-36, ed.: E. M. Gaigneaux et al.; P. H. Matter et al., J. Mol. Cat A: Chemical 264 (2007), 73-81) in each case disclose a typical embodiment of processes for obtaining such nitrogen-doped carbon nanotubes. Van Dommele et al. further disclose that the basic catalysts obtained can be suitable for processes in fine chemicals. Neither discloses that the catalysts disclosed can be used in processes for hydrogenating organic compounds nor that particular arrangements of the nitrogen in such nitrogen-doped carbon nanotubes can be particularly advantageous for such hydrogenations.

WO 2005/035841 discloses that catalysts comprising nitrogen-doped carbon nanotubes are catalytically active for the reduction of oxygen. In this context, it is further disclosed that such catalysts comprising nitrogen-doped carbon nanotubes have a better catalytic activity for the reduction of hydrogen peroxide than undoped carbon nanotubes. It is not disclosed that hydrogenation using the catalysts is possible nor which particular arrangements of the nitrogen in such nitrogen-doped carbon nanotubes could be particularly advantageous for this purposes.

Proceeding from the known prior art, it is therefore an object of the invention to provide a catalyst and a process using such a catalyst which allows hydrogenation of organic compounds without the use of expensive noble metals as catalytically active component for the hydrogenation. The novel catalyst should also not comprise any pyrophoric catalytically active components so that the novel process can dispense with the use thereof.

It has surprisingly been found that this object can be achieved for the first time and in a particularly advantageous way by the novel catalysts and process using these catalysts disclosed here.

The present invention therefore firstly provides a catalyst for hydrogenating organic compounds, which comprises nitrogen-doped carbon nanotubes as catalytically active component and is characterized in that the proportion of nitrogen in the nitrogen-doped carbon nanotubes is in the range from 0.05 to 20% by weight in the graphitic layers and in that the nitrogen is present at least partly in a pyridinic arrangement.

The catalyst of the invention preferably comprises nitrogen-doped carbon nanotubes having a nitrogen content of from 0.1% by weight to 18% by weight and particularly preferably from 0.5% by weight to 16% by weight in the graphitic layers.

The proportions of nitrogen in the nitrogen-doped carbon nanotubes are particularly advantageous because it has surprisingly been found that there is an optimum of the nitrogen content of the nitrogen-doped carbon nanotubes for the hydrogenation of organic compounds. Proceeding from the prior art, it will have been obvious to presume that a further increase in the nitrogen content would be associated with a further-improved catalytic activity of the nitrogen-doped carbon nanotubes. In contrast, the optimum in the abovementioned range has surprisingly been found.

The proportion of nitrogen present in the nitrogen-doped carbon nanotubes can be present not only as at least a proportion of pyridinic nitrogen but also in the form of quaternary nitrogen and/or nitro nitrogen and/or nitroso nitrogen and/or amine nitrogen.

The proportions of nitro and/or nitroso and/or amine nitrogen are of subordinate importance to the present invention insofar as their presence does not significantly hinder the invention as long as the above-described proportions and ratios in respect of pyridinic and/or quaternary nitrogen are present.

The proportion of pyridinic nitrogen in the catalyst of the invention is preferably at least 20 mol % of the nitrogen present in the nitrogen-doped carbon nanotubes. The proportion is particularly preferably greater than 30 mol %.

Likewise, the ratio of pyridinic nitrogen to quaternary nitrogen is preferably at least 1.25 mol/mol, particularly preferably at least 1.3 mol/mol.

The proportions and ratios indicated are particularly advantageous because it has surprisingly been found that the pyridinic nitrogen in particular has a particularly strong influence on the catalytic activity of the catalyst for the hydrogenation of organic compounds.

Without laying claim to a complete and particular theory, it can be presumed that the symmetrical carbon-stabilized arrangement of the nitrogen in the pyridinic arrangement particularly advantageously forms a stabilizing intermediate complex with hydrogen which is therefore more readily available as reactive species to the hydrogenation of the organic material to be hydrogenated. In the case of quaternary nitrogen, steric hindrance could be presumed, while the abovementioned other forms of nitrogen in the nitrogen-doped carbon nanotubes are not symmetrically stabilized and can therefore not form a stabilizing intermediate complex with hydrogen.

In a preferred variant, the nitrogen-doped carbon nanotubes are subjected to washing with a mineral or organic acid such as HCl, $H_2SO_4$, etc.

Such washing is advantageous since residual constituents of the catalyst by means of which the nitrogen-doped carbon nanotubes are produced are removed thereby and secondary reactions which may take place over these residues of catalyst can be minimized as a result.

It is likewise possible for the nitrogen-doped carbon nanotubes to be present in chemically functionalized form.

Chemical functionalization is particularly advantageous since an improved interaction of the substrate to be hydrogenated with the catalytically active nitrogen-doped carbon nanotubes may be able to be induced in this way, i.e. the surface properties can be improved for the purposes of the hydrogenation reaction.

The proportion of the nitrogen-doped carbon nanotubes in the catalyst is usually at least 50% by weight. The proportion is preferably at least 80% by weight, particularly preferably at least 95% by weight.

Apart from the nitrogen-doped carbon nanotubes, the catalyst of the invention can further comprise fillers or traces of metals.

In the context of the present invention, fillers are all substances which are present as inert material together with the nitrogen-doped carbon nanotubes, i.e. all substances which are not catalytically active. Nonlimiting examples of fillers are, for instance, alumina, silica, titanium dioxide, zirconium dioxide or mixtures thereof, steatite, ceramic, glass or graphite.

In the context of the present invention, the expression "traces of metals" means a proportion of metals of less than 1% by weight of the catalyst. Possible metals which can be present in traces are the metals selected from the group consisting of Fe, Ni, Cu, W, V, Cr, Sn, Co, Mn and Mo.

These metals may or may not be catalytically active. Whether the traces of metals comprise catalytically active components is not important for the present invention. The catalytic effect according to the invention is based on the particular nitrogen-doped carbon nanotubes, not on the traces of metals.

In a preferred further development of the catalyst of the invention, the traces of metals are therefore washed out from the nitrogen-doped carbon nanotubes so that the catalyst no longer comprises any traces of metals.

Such washing-out can be effected in the form of a wet chemical purification step in which the nitrogen-doped carbon nanotubes are treated with a mineral acid, for example an acid selected from the group consisting of: HCl, $H_2SO_4$, $HNO_3$, $HClO_4$, etc. Preference is given to using HCl and $HNO_3$, very preferably HCl. The concentration of the acid is preferably from 0.1 mol/l to 36% by weight of HCl and very particularly preferably from 1 mol/l to 10 mol/l.

The present invention further provides a process for hydrogenating organic compounds by means of hydrogen, which is characterized in that the hydrogenation is carried out in the presence of a catalyst which comprises nitrogen-doped carbon nanotubes as catalytically active component, the proportion of nitrogen in the nitrogen-doped carbon nanotubes is in the range from 0.05 to 20% by weight in the graphitic layers and the nitrogen is present at least partly in a pyridinic arrangement.

Organic compounds are, in the context of the present invention, all substances which have at least one hydrogenation-active functional group. Which chemical groups can be referred to as hydrogenation-active functional groups is generally known to those skilled in the art. Nonlimiting examples are nitro groups, C—C double bonds, C—C triple bonds, aromatic rings, carbonyl groups, nitrile groups, ester groups, diolefins, etc.

The process of the invention can either be carried out so that the organic compound and the hydrogen are present in gaseous form or so that the organic compound is present in a liquid phase and the hydrogen is present in gaseous form.

If the organic compound is present in a liquid phase, the liquid phase can be formed by the organic compound itself or the organic compound can be present in a liquid solvent.

If the organic compound is present in a solvent, the solvent can be an organic solvent or water. The solvent is preferably an organic solvent. It is particularly preferably an organic solvent which does not comprise any hydrogenation-active functional group or a mixture of such organic solvents Nonlimiting examples of organic solvents which can be used for the alternative embodiment of the invention are unsubstituted or substituted aromatic or nonaromatic hydrocarbons having an alkyl radical or halogen as substituent. Preference is given to alkanes, haloalkanes, alcohols and ethers. Particularly preference is given to hexane, methylcyclohexane, heptane, methanol, ethanol and i-propanol.

The organic compound is usually present in the solvents in proportions of from 0.1% by weight to 60% by weight, preferably from 1% by weight to 55% by weight and particularly preferably from 2.5% by weight to 50% by weight.

The temperatures at which the hydrogenations in the presence of a liquid phase comprising the organic compound are carried out are usually in the range from 20° C. to 350° C., preferably in the range from 40° C. to 300° C.

The upper limit is determined by safety considerations. The process of the invention is not actually limited here. The lower limit is at temperatures at which, despite the high activity of the catalyst used, the low conversions and space-time yields make the process uneconomical.

The total pressure for carrying out hydrogenations in the presence of a liquid phase comprising the organic compound is usually from 1 bar to 300 bar, preferably from 1 bar to 200 bar, particularly preferably from 1 bar to 50 bar.

Here too, safety considerations define the upper limit. The process of the invention is not actually limited thereby. The lower limit is at pressures at which, despite the high activity of the catalyst used, the low conversions and space-time yields make the process uneconomical.

The partial pressure percentage of hydrogen in hydrogenations in the presence of a liquid phase comprising the organic compound, expressed as the percentage of the total pressure in the process made up by the hydrogen partial pressure, can be in the range from 50 to 100%. It is preferably above 70%, particularly preferably above 90%.

The apparatuses in which such a process can be carried out are the reaction apparatuses which are generally known to those skilled in the art under the generic terms, for instance a stirred vessel (slurry reactor), nozzle reactor, bubble column, trickle-bed reactor, membrane reactor, etc.

If the organic compound is present in the gas phase, the process can, in this alternative embodiment, be carried out at temperatures in the range from 120 to 750° C., preferably from 140 to 650° C., particularly preferably from 200 to 600° C.

The absolute reaction pressure in the presence of the organic compound in gaseous form is usually in the range from 1 to 100 bar, preferably from 1.2 to 75 bar, particularly preferably from 1.5 to 50 bar.

The apparatuses in which such a process can be carried out are the reaction apparatuses generally known to those skilled in the art under the generic terms, for instance fixed-bed or fluidized-bed reactors and also shell-and-tube reactors.

Regardless of whether the organic compound is present in a liquid phase or in a gaseous form, the process of the invention can be carried out adiabatically or isothermally or approximately isothermally. It is preferably carried out approximately isothermally.

Furthermore, it can be carried out continuously or batchwise. It is preferably carried out continuously.

Or once again independently of this, the process can be carried out in one or more stages.

In a preferred further development of the process, from 2 to 10, preferably from 2 to 6, particularly preferably from 2 to 5, in particular 2 or 3, reaction zones connected in series can be present, with cooling zones being able to be provided between them if appropriate.

The hydrogen can be introduced either entirely together with the organic compound upstream of the first reaction zone or its introduction can be distributed over the various reaction zones. This series arrangement of individual reaction zones can be present within one of the above-disclosed reaction apparatuses or be distributed over individual reaction apparatuses.

The catalyst used in the process of the invention preferably comprises nitrogen-doped carbon nanotubes which have a nitrogen content of from 0.1% by weight to 20% by weight, particularly preferably from 0.5% by weight to 18% by weight, in the graphitic layers.

The proportion of the nitrogen in the nitrogen-doped carbon nanotubes which is present as pyridinic nitrogen is likewise preferably at least 20 mol %. The proportion is particularly preferably greater than 30 mol %.

Furthermore, the ratio of pyridinic nitrogen to quaternary nitrogen in the nitrogen present in the nitrogen-doped carbon nanotubes is preferably at least 1.25 mol/mol, particularly preferably at least 1.3 mol/mol.

The catalyst can be present as loose material or as a fixed bed. The catalyst is preferably present as a fixed bed.

In a preferred further development of the process of the invention, the catalyst is present as a fixed bed in the form of a structured bed in which the catalyst activity increases in the main flow direction in the reaction zone.

Such a structured bed can preferably be achieved by a differing content of nitrogen-doped carbon nanotubes in the catalyst of the invention or by different dilution with an inert material or by use of catalysts comprising different proportions of quaternary nitrogen in the nitrogen-doped carbon nanotubes.

In a further preferred embodiment of the process, the catalyst is present as shaped bodies in the reaction zone. In this further preferred embodiment, too, dilution with inert material can be provided. If such dilution with inert material is provided, the inert material is preferably present in the form of shaped bodies similar to the catalyst alongside the catalyst.

In the context of the present invention, shaped bodies are geometric bodies which are made of the abovementioned materials and have any, predefined shapes, as can be obtained, for example, by pressing. Preferred shaped bodies are pellets, rings, cylinders, stars, wagon wheels or spheres. Particular preference is given to spheres, rings, cylinders or star extrudates.

The size of the shaped bodies is usually in the range from 500 µm to 5 mm and very particularly preferably from 1 to 3 mm If the organic compound is present in a liquid phase, it is also possible, in an alternative embodiment of the process of the invention, to use a fine powder of the catalyst. The powder is preferably used in a particle size of 10-1000 µm, preferably 100-900 µm.

The process of the invention surprisingly and advantageously allows the heterogeneously catalyzed hydrogenation of organic compounds with a high conversion, selectivity and yield and dispenses with the use of expensive noble metals or pyrophoric catalyst constituents.

The process of the invention will be illustrated below with the aid of examples which do not, however, constitute a restriction of the inventive concept.

EXAMPLES

Example 1

Production of Nitrogen-Doped Carbon Nanotubes 72 g of a Co—Mn—Al—Mg mixed oxide catalyst (Mn:Co:$Al_2O_3$:MgO 17:18:44:22), produced as described, for example, in WO 2007/093337, example 2, were placed in a fluidized-bed reactor in which an initial charge of 350 g of conventional carbon nanotube agglomerates (Baytubes®, from Bayer MaterialScience AG) was already present in order to achieve uniform distribution of the gas stream and the temperature in the fluidized bed.

The particles of the Co—Mn—Al—Mg mixed oxide catalyst had a diameter in the range from 32 µm to 90 µm. The reactor was externally heated electrically to a reaction temperature of 750° C. and, after nitrogen had been passed through (making inert), the reaction mixture consisting of 15 g/min of acetonitrile, 25 standard l/min of nitrogen and 3.6 standard l/min of hydrogen was introduced into the fluidized-bed reactor through a perforated plate at the lower end of the reactor.

The feed gas mixture was produced in an upstream electrically heated fixed bed (diameter 50 mm, height 1000 mm, filled with glass Raschig rings). The acetonitrile was introduced in liquid form into this bed by means of a metering pump; the nitrogen and the hydrogen were added in gaseous form to the vaporizing acetonitrile in such a way that a superheated gas mixture having a temperature of 200° C. left the fixed bed and entered the fluidized-bed reactor.

In the fluidized bed, nitrogen-doped carbon nanotubes formed on the Co—Mn—Al—Mg mixed oxide catalyst, as a result of which the catalyst particles were broken open and the agglomerate particles of nitrogen-doped carbon nanotubes and catalyst residues were formed.

The catalyst was supplied with the feed gases for a period of 90 minutes until the catalyst had been completely deactivated. The activity of the catalyst was monitored by the evolution of hydrogen in the reactor, determined by means of gas chromatography. The point in time at which the evolution of hydrogen in the process had been reduced by a factor of at least 10 compared to the initially measured value was taken as the point in time of complete deactivation.

After making the reactor inert again, 220 g of a black powder were taken from the reactor; a further about 350 g of product remained in the reactor as initial bed for the next batch. This procedure is repeated 3 times until the entire carbon nanotube bed has been replaced.

The amount of carbon present in the nitrogen-doped carbon nanotubes produced divided by the mass of catalyst used will hereinafter be referred as the productivity.

A productivity of 7.6 g of nitrogen-doped carbon nanotubes/g of catalyst was achieved.

The nitrogen-doped carbon nanotubes produced in this way were finally washed under reflux with 2 mol/l of HCl for 3 hours.

The nitrogen present in the nitrogen-doped carbon nanotubes was determined by means of elemental analysis (Trustec instrument, from LECO, method according to the manufacturer's instructions). The nitrogen content was 5.0% by weight.

The different bonding states of the nitrogen and the quantification of these were determined by means of ESCA analysis (ThermoFisher, ESCALab 220iXL; method according to the manufacturer's instructions). The ratio of pyridinic nitrogen to quaternary nitrogen in the nitrogen-doped carbon nanotubes obtained was 0.81 mol/mol.

Example 2

Production of Nitrogen-Doped Carbon Nanotubes

These were produced as in example 1 except that acetonitrile was fed into the reactor at a feed rate of 19 g/min The productivity was 5.9 g of nitrogen-doped carbon nanotubes/g of catalyst.

The nitrogen-doped carbon nanotubes produced in this way had a nitrogen content of 4.1% by weight and a ratio of pyridinic nitrogen to quaternary nitrogen of 1.31 mol/mol.

Example 3

Production of Nitrogen-Doped Carbon Nanotubes

These were produced as in example 1 except that the weight of catalyst introduced was 48 g and pyridine instead of acetonitrile was fed into the reactor at a feed rate of 26 g/min The productivity was 10.1 g of nitrogen-doped carbon nanotubes/g of catalyst.

The nitrogen-doped carbon nanotubes produced in this way had a nitrogen content of 4.4% by weight and a ratio of pyridinic nitrogen to quaternary nitrogen of 1.15 mol/mol.

Example 4

Production of Nitrogen-Doped Carbon Nanotubes

These were produced as in example 3 except that the weight of catalyst introduced was 104 g. The productivity was 13.8 g of nitrogen-doped carbon nanotubes/g of catalyst.

The nitrogen-doped carbon nanotubes produced in this way had a nitrogen content of 7.7% by weight and a ratio of pyridinic nitrogen to quaternary nitrogen of 0.59.

Example 5

Production of Nitrogen-Doped Carbon Nanotubes

These were produced as in example 3 except that the weight of catalyst introduced was 80 g and dimethylformamide instead of pyridine was fed into the reactor at a feed rate of 31.5 g/min and no hydrogen was introduced.

The productivity was 4.2 g of nitrogen-doped carbon nanotubes/g of catalyst. The nitrogen-doped carbon nanotubes produced in this way had a nitrogen content of 3.1% by weight and a ratio of pyridinic nitrogen to quaternary nitrogen of 1.39 mol/mol.

Example 6

Production of Nitrogen-Doped Carbon Nanotubes

These were produced as in example 5 except that the feed rate was set to 10.1 g/min The productivity was 5.0 g of nitrogen-doped carbon nanotubes/g of catalyst. The nitrogen-doped carbon nanotubes produced in this way had a nitrogen content of 3.5% by weight and a ratio of pyridinic nitrogen to quaternary nitrogen of 1.52 mol/mol.

TABLE 1

Composition and properties of the catalysts as per examples 1-6

| Ex. [—] | Nitrogen content [% by weight] | Pyr./Quat. [mol/mol] |
|---|---|---|
| 1 | 5.0% | 0.81 |
| 2 | 4.1% | 1.31 |
| 3 | 4.4% | 1.15 |
| 4 | 7.7% | 0.59 |
| 5 | 3.1% | 1.39 |
| 6 | 3.5% | 1.52 |

Examples 7-13

Hydrogenation of Nitrobenzene 5 g of a reaction mixture composed of a 30% strength solution of nitrobenzene in isopropanol were placed in a stirred pressure reactor. The nitrogen-doped carbon nanotubes from examples 1-6 or undoped carbon nanotubes (Baytubes®, from Bayer MaterialScience AG) were in each case added thereto in such an amount that the carbon nanotubes amounted to 3% by weight of the suspension.

The hydrogenation was in all cases carried out at 150° C., 40 bar and a stirrer speed of 1000 rpm in the above-described pressure reactor.

After 120 minutes, the reaction was stopped by cooling the pressure reactor to room temperature (23° C.) and the reaction mixture was, after the nitrogen-doped carbon nanotubes had been separated off, subjected to a gas-chromatographic analysis (instrument: Hewlett Packard HP6890, column DB-5, 30 m; according to the manufacturer's instructions). The proportions of aniline in the reaction mixtures analyzed in each case are summarized in table 2 for the various catalysts as per examples 1-6 and also for the undoped carbon nanotubes.

TABLE 2

Composition of the reaction mixtures and catalysts as per examples 7-13

| Ex. [—] | Catalyst | Aniline [% by area] |
|---|---|---|
| 7 | as per ex. 1 | 31 |
| 8 | as per ex. 2 | 79 |
| 9 | as per ex. 3 | 65 |
| 10 | as per ex. 4 | 19 |
| 11 | as per ex. 5 | 98 |
| 12 | as per ex. 6 | 100 |
| — | Baytubes ® | 0.4 |

It can be seen that, in particular, the nitrogen-doped carbon nanotubes which have a ratio of pyridinic nitrogen to quaternary nitrogen of greater than 1 have a particularly high catalytic activity and accordingly have a particularly high proportion of aniline in the reaction product after reaction in the process of the invention.

In addition, a surprising almost linear correlation between the ratio of pyridinic nitrogen to quaternary nitrogen and the achievable conversion into aniline is found.

The invention claimed is:

1. A process for hydrogenating organic compounds by means of hydrogen comprising hydrogenating the organic compound in the presence of a catalyst, said catalyst comprising nitrogen-doped carbon nanotubes as catalytically active component, wherein said nanotubes are present as an agglomerate with Co—Mn—Al—Mg mixed oxide catalyst, and the proportion of nitrogen in the nitrogen-doped carbon nanotubes is in the range from 0.05 to 20% by weight in graphitic layers and the nitrogen is present at least partly in a pyridinic arrangement, wherein the organic compound is a nitroaromatic substrate.

2. The process as claimed in claim 1 wherein the organic compound is present in a liquid phase and the hydrogen in the present in gaseous form.

3. The process as claimed in claim 2 wherein the organic compound is present in a liquid solvent.

4. The process as claimed in claim 3 wherein the solvent is an organic solvent which does not comprise any hydrogenation-active functional group or is a mixture of such organic solvents.

5. The process as claimed in claim 2 wherein the process is carried out at temperatures in the range from 20° C. to 350° C.

6. The process as claimed in claim 1 wherein the organic compound and the hydrogen are present in gaseous form.

7. The process as claimed in claim 1 wherein the process is carried out at temperatures of from 120 to 750° C.

8. The process as claimed in claim 1 wherein the process is carried out in a plurality of stages reaction zones connected in series.

9. The process as claimed in claim 1 wherein the catalyst contains at least 50% by weight of nitrogen-doped carbon nanotubes.

10. The process as claimed in claim 1 wherein the catalyst is present as a fixed bed.

11. The process as claimed in claim 10 wherein the fixed bed is present in the form of a structured bed in which the catalyst activity increases in the main flow direction in the reaction zone.

12. The process as claimed in claim 8 wherein the process is carried out in 2-3 reaction zones.

13. The process as claimed in claim 9 wherein the catalyst contains at least 95% by weight of nitrogen-doped carbon nanotubes.

14. The process as claimed in claim 7 wherein the process is carried out at temperatures of from 200 to 600° C.

15. The process as claimed in claim 1 wherein the organic compound is nitrobenzene.

* * * * *